(12) United States Patent
Tanaka

(10) Patent No.: US 6,685,650 B2
(45) Date of Patent: Feb. 3, 2004

(54) FUNDUS BLOOD FLOWMETER

(75) Inventor: Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 10/180,596

(22) Filed: Jun. 26, 2002

(65) Prior Publication Data

US 2003/0018275 A1 Jan. 23, 2003

(30) Foreign Application Priority Data

Jun. 27, 2001 (JP) ........................................ 2001-194166

(51) Int. Cl.[7] .............................. A61B 5/02; A61B 3/50
(52) U.S. Cl. ...................... 600/504; 600/481; 600/476; 600/479; 351/221
(58) Field of Search ................................ 600/504, 481, 600/483, 476, 479, 480; 351/221, 216

(56) References Cited

U.S. PATENT DOCUMENTS 6,324,420 B1 * 11/2001 Kishida et al. ............. 600/479
6,337,993 B1 * 1/2002 Kishida et al. ............. 600/476
6,411,839 B1 * 6/2002 Okinishi ..................... 600/479

* cited by examiner

Primary Examiner—Max F. Hindenburg
Assistant Examiner—Navin Natnithithadha
(74) Attorney, Agent, or Firm—Morgan & Finnegan, L.L.P.

(57) ABSTRACT

When a blood flow velocity in a blood vessel on the fundus is to be measured, a cofocal aperture is inserted to eliminate the influence of scattered light from regions other than a measurement region, thereby obtaining a measurement result with a high S/N. When a blood flow velocity in the papilla is to be measured, a light shielding aperture is inserted in place of the cofocal aperture to eliminate a regularly reflected component from the papilla, thereby obtaining a measurement result with a high S/N. A fundus blood flowmeter can select one of the two measuring modes and can switch the above apertures in accordance with each mode.

4 Claims, 7 Drawing Sheets

FUNDUS BLOOD FLOWMETER

BACKGROUND OF THE INVENTION

1. Field of the Invention

The present invention relates to a fundus blood flowmeter for measuring a blood flow velocity on the basis of scattered/reflected light from a fundus portion upon irradiation of the fundus portion with a laser beam.

2. Description of Related Art

Fundus blood flow measurement methods include a method called Laser Doppler Velocimetry (LDV) for measuring an intravascular blood flow velocity and a method called Laser Doppller Flowmetry (LDF) for measuring a blood flow velocity at an optical nerve head (papilla). A technique of allowing one apparatus to execute these two methods is disclosed in, for example, Japanese Patent Application Laid-Open No. 7-136141.

In LDV, measurement light from a measurement light source illuminates a fundus blood vessel in the form of a point, and scattered/reflected light is received by two light-receiving elements such as photomultipliers placed on two light-receiving optical paths defining a predetermined angle. Each light reception signal contains a predetermined beat signal generated by interference between a component Doppler-shifted by blood flowing in a blood vessel Ev and a component reflected by a still blood vessel wall. A blood flow velocity in the blood vessel is obtained by frequency-analyzing this beat signal.

FIG. 10 shows an example of the result obtained by frequency-analyzing a light reception signal obtained by a photomultiplier. Referring to FIG. 10, the abscissa represents a frequency $\Delta f$, and the ordinate represents, an output $\Delta S$. The relationship between a maximum frequency $\Delta f max$, a frequency vector $\kappa i$, a frequency vector $\kappa s$ in the light-receiving direction, and a blood flow velocity vector $v$ is expressed by $$\Delta f max = (\kappa s - \kappa i) \cdot v \quad (1)$$

If, therefore, equation (1) is modified by using maximum frequencies $\Delta f max1$ and $\Delta f max2$ calculated from the light reception signals from the respective photomultipliers, a wavelength $\lambda$ of a laser beam, a refractive index $n$ of a measurement region, an angle $\alpha$ defined by the light-receiving optical paths within the eye, and an angle $\beta$ defined by a plane formed by the incidence optical paths in the eye and the blood flow velocity vector, a maximum blood flow velocity $V max$ can be given by $$V max = \lambda \cdot |\Delta f max1 - \Delta f max2| / (n \cdot \alpha \cdot \cos \beta) \quad (2)$$

Such measurements in two directions cancel out the contribution of measurement light in the incidence direction. This makes it possible to measure a blood flow at an arbitrary region on the fundus. In order to measure a true blood flow velocity from the relationship between the nodal line defined by the plane formed by two light-receiving optical paths and the fundus and the angle $\beta$ defined by the blood flow velocity vector $v$ and a nodal line A, the nodal line must be matched with the velocity vector $v$ and $\cos \beta = 1$ must be set. For this purpose, the overall light-receiving optical system is rotated or an image rotator is placed in the light-receiving optical system to optically match them with each other.

As an apparatus having a cofocal aperture to eliminate the influence of a blood flow in the choroid during measurement by LDV, the apparatus disclosed in Japanese Patent Application Laid-Open No. 7-79934 is known. Note that an example of measurement of a blood flow velocity in a blood vessel on the fundus is described in Feke, IEEE Transactions of Biomedical Engineering, Vol BME-34, No. 9, September 1987, pp. 673–680 and the like.

In contrast to this, when a blood flow velocity at the papilla is to be measured by LDF, measurement light is applied to the papilla. The light reflected by the papilla is received by a photomultiplier as a light-receiving element. In this case, blood flow velocity vectors, other than the one in a fundus blood vessel in the papilla, have irregular directions, and hence the scattering/reflecting directions of measurement light also become irregular. For this reason, it is said that only one light-receiving direction will suffice. A blood flow velocity at the papilla is obtained by frequency-analyzing this light reception signal.

FIG. 11 shows an example of the result obtained by frequency-analyzing a light reception signal from a blood flow in the papilla. Referring to FIG. 11, the abscissa represents a frequency $\Delta f$; and the ordinate represents, an output $S$. The relationship between the frequency $\Delta f$ and the output $S$ can be expressed by an approximate expression like equation (3) given below, and is represented by the thick solid line in FIG. 11.

$$S(\Delta f) = -K \cdot \log(\Delta f / \gamma) \quad (3)$$

If equation (3) is modified by using a wavelength $\lambda$ of a laser beam, a maximum blood flow velocity $V max$ in the papilla can be given by $$V max = \gamma \cdot \lambda / 2 \quad (4)$$

As indicated by equation (4), unlike in measurement of a blood flow velocity in a blood vessel, a blood flow velocity in the papilla can be measured regardless of the angle defined by a blood flow and a velocity vector because a measurement light beam is scattered/reflected by a blood flow in the papilla in various directions. Note, however, only a relative velocity is obtained in this case. An example of measurement of a blood flow velocity in the papilla is described in Sebag, et al., Investigative Ophthalmology & Visual Science, Vol 26, No. 10, October 1985, pp. 1415–1422.

In the prior art described above, however, in LDF in which a blood flow velocity in the papilla is measured, a light reception signal received by the photomultiplier contains not only a scattered/reflected component from the papilla but also a regularly reflected component. Consequently, the S/N of an AC component required for frequency analysis is poor.

With ocular movement during measurement, the regularly reflected component from the papilla fluctuates, and the coincidence with approximate expression (4) may become worse in frequency analysis.

SUMMARY OF THE INVENTION

It is an object of the present invention to provide a fundus blood flowmeter which solves the above problem and can easily and accurately measure a blood flow velocity at the fundus.

In order to achieve the above object, the present invention is characterized by including an irradiation system which irradiates the fundus with coherent measurement light, a detector which detects scattered light from the fundus upon irradiation of the measurement light, a processor which calculates a blood flow velocity by frequency-analyzing a signal from the detector, and a light shielding aperture which is placed to cover a region irradiated with the measurement light on a plane of the detector which is nearly conjugate to the fundus.

A cofocal aperture which transmits scattered light from the irradiated region and its peripheral portion may be selectively inserted into an optical path in place of the light shielding aperture. In addition, control may be performed such that in the first mode of measuring blood flow information about the papilla, the light shielding aperture may be inserted, whereas in the second mode of measuring a blood flow velocity in a blood vessel on the fundus, the cofocal aperture may be inserted.

DETAILED DESCRIPTION OF THE PREFERRED EMBODIMENT

The present invention will be described in detail hereinafter based on the illustrated embodiment.

Figure 1:
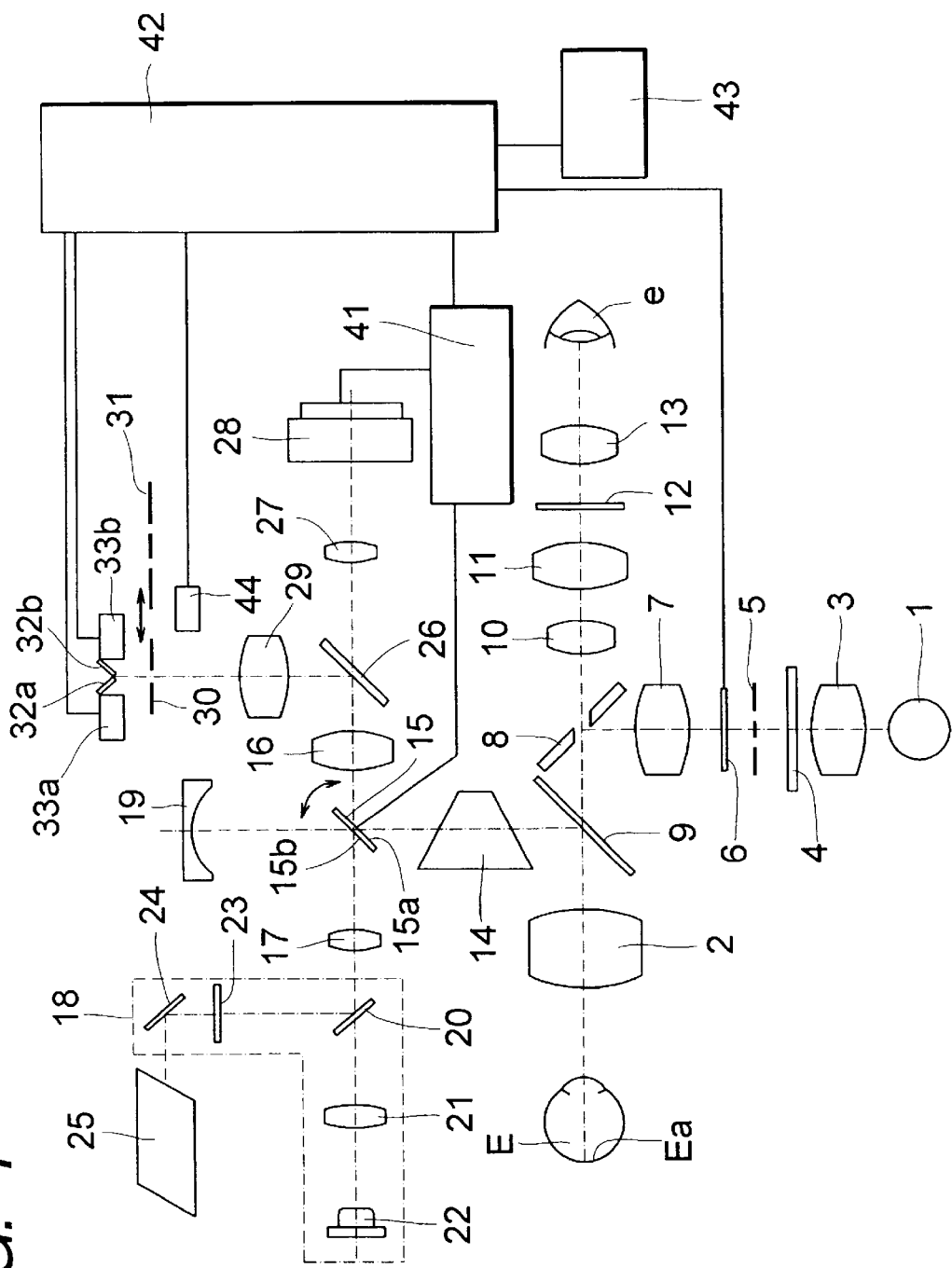
FIG. 1 is a view showing the arrangement of the first embodiment.

FIG. 1 shows the overall arrangement of a fundus blood flowmeter of the embodiment. On an illumination optical path extending from an observation light source 1 formed from, e.g., a tungsten lamp for emitting white light, to an objective lens 2 that opposes an eye E of a patient to be examined, a condenser lens 3, a field lens 4 with a bandpass filter that transmits only wavelength light in, e.g., the yellow wavelength range, a ring slit 5 which is set at a position nearly conjugate to the pupil of the eye E, a transmission liquid crystal panel 6 serving as a fixation target display element which is placed at a position nearly conjugate to the fundus of the eye E so as to be movable along the optical path, a relay lens 7, an apertured mirror 8, and a bandpass mirror 9 which transmits wavelength light in the yellow wavelength range and reflects most of other light beams, are sequentially arranged. A focusing lens 10, relay lens 11, scale plate 12, and eyepiece 13, which constitute a fundus observation optical system and are movable along the optical path, are sequentially arranged behind the apertured mirror 8 up to an eye e of an operator.

On the optical path in the reflecting direction of the bandpass mirror 9, an image rotator 14 and a galvanometric mirror 15 having both lower and upper reflection surfaces polished and a rotation axis perpendicular to the drawing surface are disposed. A second focus lens 16 is placed in the reflecting direction of a lower reflection surface 15a of the galvanometric mirror 15. A lens 17 and a focus unit 18 which is movable along the optical path are placed in the reflecting direction of the upper reflection surface 15b. Note that the front focal plane of the lens 17 is conjugate to the pupil of the eye E, and the galvanometric mirror 15 is located on this focal plane. A concave mirror 19 is placed behind the galvanometric mirror 15 to form a relay optical system for guiding the light beam reflected by the upper reflection surface 15b of the galvanometric mirror 15 to the image rotator 14 through a portion where the galvanometric mirror 15 is not present.

In the focus unit 18, a dichroic mirror 20 and condenser lens 21 are sequentially arranged on the same optical path as that of the lens 17, and a mask 23 and mirror 24 are arranged on the optical path in the reflecting direction of the dichroic mirror 20. The focus unit 18 is designed to be integrally movable on the optical axis.

A measurement laser diode 22 that emits coherent red light is placed on the optical path in the incidence direction of the condenser lens 21. In addition, a tracking light source 25 that emits, e.g., high-luminance green light, which is different from the light emitted from another light source, is placed on the optical path in the incidence direction of the mirror 24.

On the optical path in the reflecting direction of the lower reflection surface 15a of the galvanometric mirror 15, a focusing lens 16 that is movable along the optical path, a dichroic mirror 26, an enlargement lens 27, and a linear CCD 28 with an image intensifier are sequentially arranged to form a blood vessel detection system. On the optical path in the reflecting direction of the dichroic mirror 26, an imaging lens 29, a cofocal aperture 30 and light shielding aperture 31 that are selectively inserted into the optical path, a pair of mirrors 32a and 32b, and photomultipliers 33a and 33b are arranged to form a measurement light-receiving optical system. In intravascular blood flow measurement, the cofocal aperture 30 is inserted, whereas in papilla blood flow measurement, the light shielding aperture 31 having a size that almost blocks measurement light on the fundus is inserted. The pair of mirrors 32a and 32b are located at positions nearly conjugate to the pupil of the eye E and define the direction of a received light beam.

Figure 2:
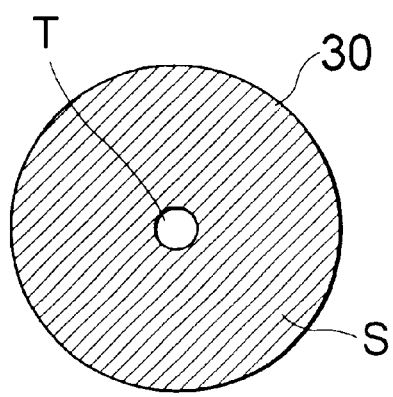
FIG. 2 is a front view of a cofocal aperture.
Figure 3:
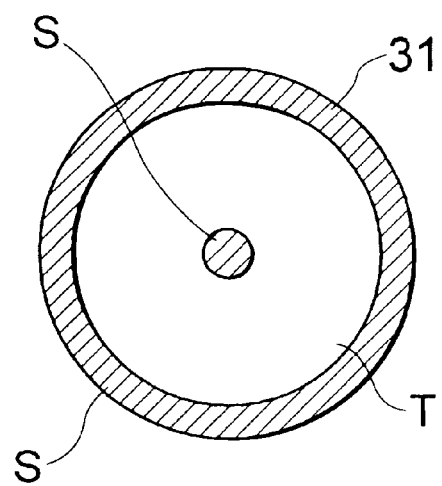
FIG. 3 is a front view of a light shielding aperture.

The cofocal aperture 30 is designed to selectively receive scattered light from a desired blood vessel Ev, and constituted by a light-transmitting portion T which has an area almost equal to or several times larger than a measurement beam and is formed near the center and a light shielding portion S formed around the light-transmitting portion T, as shown in FIG. 2. As shown in FIG. 3, the light shielding aperture 31 has a light shielding portion S which has a size almost equal to or several times larger than a measurement beam and is formed near the center, a ring-like light shielding portion S formed therearound, and a light-transmitting portion T formed between the light shielding portions S.

The output from the linear CCD 28 is connected, through a blood vessel position detection circuit 41, to a system controller 42 for controlling the overall apparatus. An input device 43 including a measuring mode switch, the outputs of the photomultipliers 33a and 33b, and an aperture switching mechanism 44 for switching between the cofocal aperture 30 and the light shielding aperture 31 are connected to the system controller 42. In addition, the output of the blood vessel position detection circuit 41 is connected to the galvanometric mirror 15.

Figure 4:
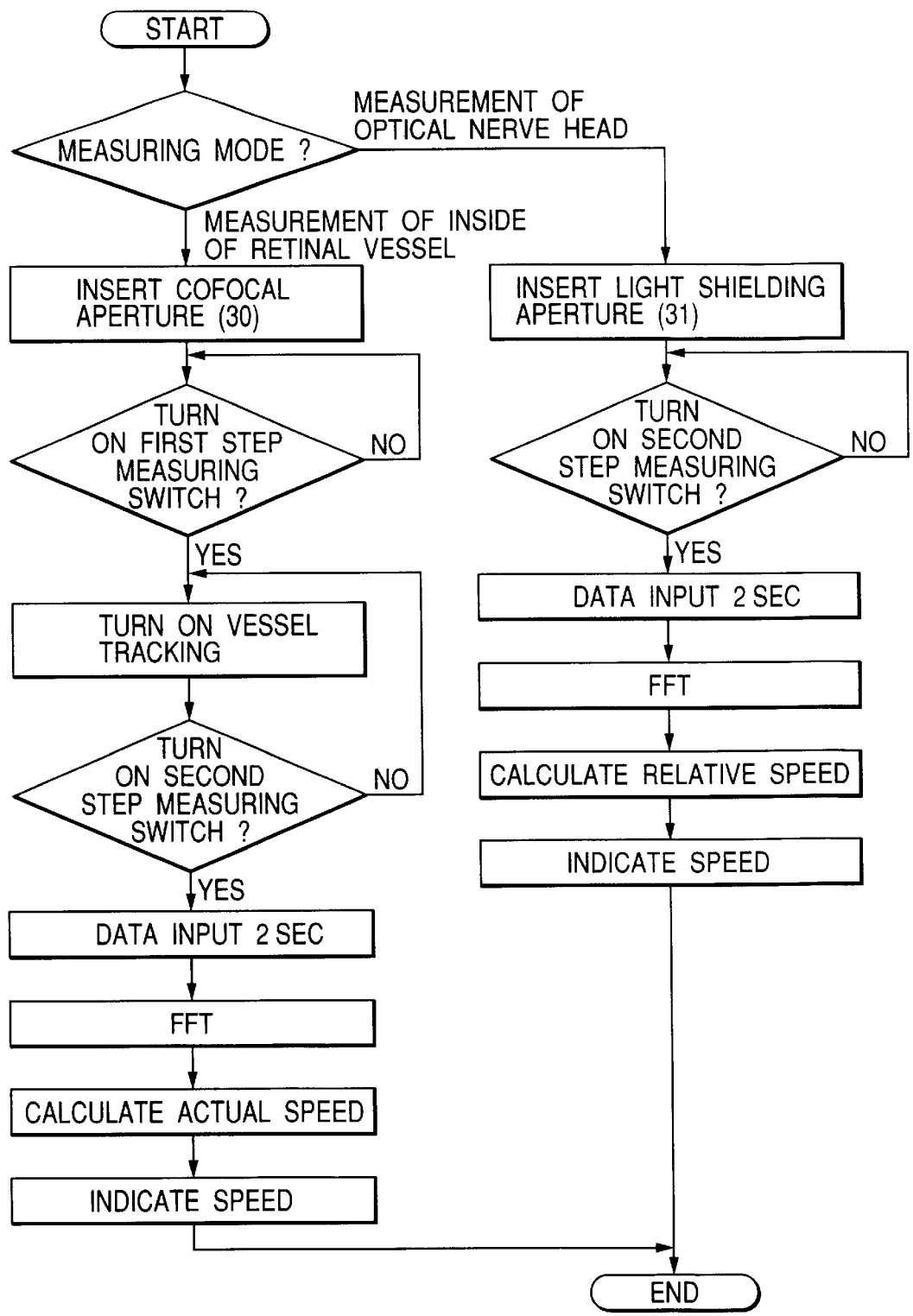
FIG. 4 is a flow chart showing operation.

FIG. 4 is a flow chart showing a method of measuring a blood flow velocity. Prior to measurement, the operator selects one of measuring modes for intravascular blood flow measurement and papilla blood flow measurement and inputs a corresponding command to the system controller 42 through the input device 43.

In intravascular blood flow measurement, the cofocal aperture 30 is inserted into the optical path by the aperture switching mechanism 44. The white light emitted from the observation light source 1 passes through the condenser lens 3, and only yellow wavelength light is transmitted through the field lens 4 with the bandpass filter. The yellow wavelength light passes through the ring slit 5 and illuminates the liquid crystal panel 6 from behind. This light passes through the relay lens 7 and is reflected by the apertured mirror 8. Only the wavelength light in the yellow wavelength range is then transmitted through the bandpass mirror 9, passes through the objective lens 2, temporarily forms a fundus illumination light optical image I on the pupil of the eye E, and then nearly uniformly illuminates a fundus Ea. At this time, the liquid crystal panel 6 functions as a fixation target and is projected on the fundus Ea of the eye E with the illumination light so as to be presented as a target image on the eye E. Note that the ring slit 5 is used to split light into fundus illumination light and fundus observation light at a position in front of the eye E, and its shape is not particularly limited as long as it can form a required light shielding region.

Figure 5:
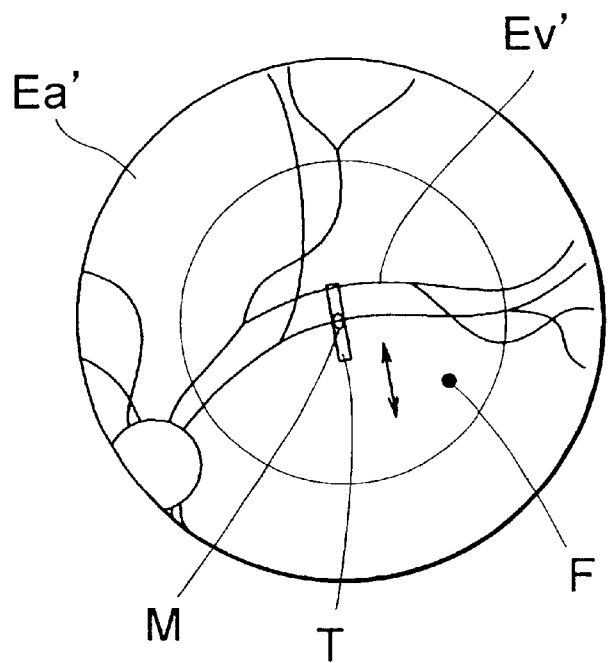
FIG. 5 is a view for explaining a fundus blood vessel image displayed on a monitor.

The reflected light from the fundus Ea returns along the same optical path to be extracted as a fundus observation light beam O from the pupil, and passes through the central aperture portion of the apertured mirror 8, focusing lens 10, and relay lens 11. The light is then formed into a fundus image Ea' on the scale plate 12. This allows the operator to observe the fundus image Ea' with the eye e through the eyepiece 13, as shown in FIG. 5.

The operator turns on the measuring switch of the apparatus to perform alignment while observing the fundus image. The measurement light emitted from the laser diode 22 is focused at a position conjugate to the fundus by the condenser lens 21 and transmitted through the dichroic mirror 20. Meanwhile, the tracking light emitted from the position detector 25 is shaped into a desired shape by the shaping mask 23 and is reflected by the dichroic mirror 20 to be superposed on the measurement light described above. In addition, the measurement light and tracking light pass through the lens 17, are reflected by the upper reflection surface 15b of the galvanometric mirror 15 once, and further reflected by the convex mirror 19 to return in the direction of the galvanometric mirror 15. In this case, the galvanometric mirror 15 is located at a position conjugate to the pupil of the eye and has the shape indicated by the dashed line in FIG. 6 on the pupil of the eye. The convex mirror 19 is concentrically placed on the optical axis to provide the function of a relay system that forms a −1× image of the surface of the galvanometric mirror 15 in cooperation with other components.

Figure 6:
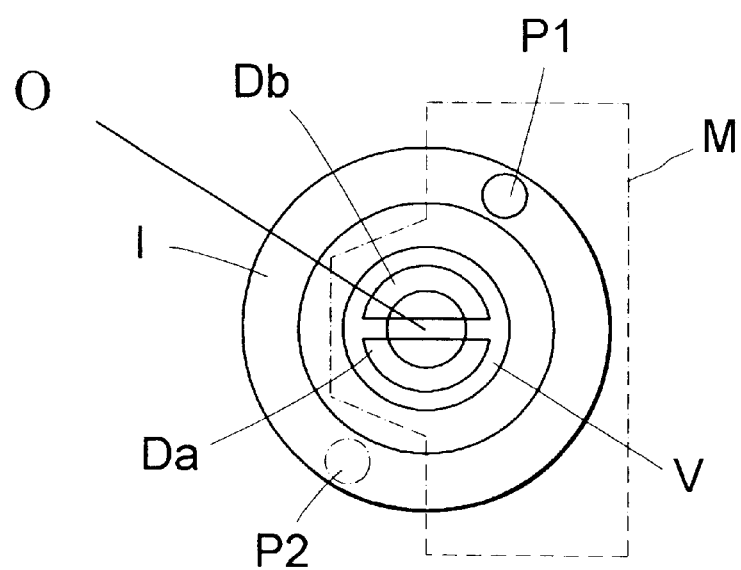
FIG. 6 is a view for explaining the positional relationship between light beams on the pupil of the eye.

FIG. 6 shows the positions of light beams on the pupil of the eye E and the outer shape of the galvanometric mirror 15. An image I of the ring slit 5 is a region illuminated with yellow illumination light. An image O of the aperture portion of the apertured mirror 8 is a fundus observation light beam. FIG. 6 also shows a received blood vessel light beam V, images Da and Db of the pair of mirrors 32a and 32b, incidence positions P1 and P2 of measurement light, and an outer shape M of the galvanometric mirror 15.

The received blood vessel light beam V is set to be larger than the fundus observation light beam O to ensure sufficient image surface illuminance on the linear CCD 28 having a larger imaging magnification than the fundus observation optical system. The influence of flare light produced on the anterior of the eye E due to an increase in the size of a light beam hardly poses a problem because the image reception range of the blood vessel image reception optical system is smaller. Although the distance between the received measurement light beams Da and Db on the pupil influences the resolution of blood flow velocity measurement, a sufficient distance can be ensured between the received measurement light beams Da and Db by increasing the received blood vessel light beam V.

The two light beams reflected at the position P1 on the back side of the image M of the galvanometric mirror 15 return to the position P2 at a notched portion of the galvanometric mirror 15 and propagate to the image rotator 14 without being reflected by the galvanometric mirror 15. The two light beams that passed through the image rotator 14 and were deflected in the direction of the objective lens 2 by the bandpass mirror 9 illuminate the fundus Ea through the objective lens 2.

The light scattered/reflected by the fundus Ea is focused on the objective lens 2 again, reflected by the bandpass mirror 9, passes through the image rotator 14, and is reflected by the lower reflection surface 15a of the galvanometric mirror 15. The light then passes through the second focus lens 16 and is split into measurement light and tracking light by the dichroic mirror 26.

The tracking light is transmitted through the dichroic mirror 26 and formed into a blood vessel image Ev', which is larger than the fundus image Ea' formed by the fundus observation optical system, on the linear CCD 28 by the enlargement lens 27. The blood vessel position detection circuit 41 generates data representing the moving amount of the blood vessel image Ev' on the basis of the blood vessel image Ev' picked up by the linear CCD 28. The system controller 42 gives the galvanometric mirror 15 the moving amount for compensating for movement through the blood vessel position detection circuit 41.

In intravascular blood flow measurement, the measurement light reflected by the dichroic mirror 26 is received by the photomultipliers 33a and 33b through the aperture portion of the cofocal aperture 30. When the operator adjusts the focus knob of the input device 43, the liquid crystal panel 6, focusing lenses 10 and 16, and focus unit 18 move along the optical path upon interlocking by a driving means (not shown). When the fundus Ea is brought into focus, all the liquid crystal panel 6, scale plate 12, linear CCD 28, and cofocal aperture 30 become nearly conjugate to the fundus Ea.

Figure 7:
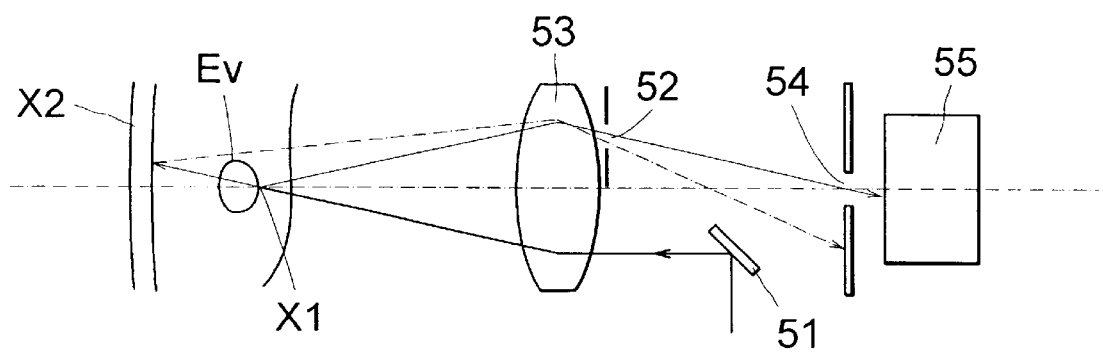
FIG. 7 is a view for explaining the function of the cofocal aperture.

This function will be described with reference to FIG. 7. X1 is the measurement region of the blood vessel Ev on the fundus Ea to be measured, and X2 is the measurement region of the pigment epithelium behind the blood vessel Ev. A light beam from the measurement laser diode 22 is incident on a mirror 51 from below and illuminates the measurement region X1 after being reflected to the left. The reflected light from the measurement region X1 passes through an opening 52 having the same function of determining a light-receiving direction as that of the pair of mirrors 32a and 32b. This light is then made to pass through a small hole 54 conjugate to the measurement region X1 by a lens 53, and is then received by a photomultiplier 55. In the above optical system, although the reflected light at the measurement region X2 which is indicated by the dotted line is formed into an image by the lens 53, like the light beam reflected at the measurement region X1 which is indicated by the solid line, this light does not strike the photomultiplier 55 because it cannot pass through the small hole 54.

In this embodiment, with the cofocal aperture 30 having the same function as that of the small hole 54 described above, the influence of scattering/reflection of measurement light from behind the blood vessel Ev, in particular, is eliminated, and only the light reflected by the blood vessel Ev at a specific depth can be received by the photomultipliers 33a and 33b. In examination, the operator sets the depth of the blood vessel Ev to be measured while watching the focused state of light on the fundus image Ea' shown in FIG. 5, and brings the fundus image Ea' into focus. Thereafter, output signals from the photomultipliers 33a and 33b are processed by the system controller 42, and a blood flow velocity on the fundus Ea is obtained by frequency analysis.

Part of the measurement light and part of the scattered/reflected light of the tracking light from the fundus Ea are transmitted through the bandpass mirror 9, guided to the fundus observation optical system behind the apertured mirror 8, and observed, together with the fundus image Ea' and a target image F, through the eyepiece 13, as shown in FIG. 5. The tracking light is formed into a bar-like indicator T on the scale plate 12, and the measurement light is formed into a spot image M on the central portion of the indicator T. The two images can be one-dimensionally moved on the fundus Ea with an operation member such as the operation lever of the input device 43. A perfect circle in the center of the visual field is a scale prepared for the scale plate 12, and indicates a range in which the indicator T can be moved.

In measurement, first of all, the operator brings the fundus image Ea' into focus. The operator then operates the input device 43 to move the target image F, moves the observation region by guiding the line of sight of the eye E, and moves the blood vessel Ev to be measured into a circle S of the scale plate 12. The operator operates the image rotator 14 with the operation lever of the input device 43 to rotate the indicator T so as to make it perpendicular to the running direction of the blood vessel Ev to be measured.

At this time, since fundus observation light has not passed through the image rotator 14, the operator recognizes that only the indicator T rotates. As a consequence, an image of each optical member on the pupil shown in FIG. 6 rotates about the origin in the same direction and through the same angle, and a straight line connecting the centers of the received measurement light beams Da and Db coincides with the running direction of the blood vessel Ev. This operation is equivalent to setting $\beta=0°$ in equation (2) for velocity calculation described in the prior art.

When the fundus Ea moves in a direction perpendicular to the running direction, a light beam from the laser diode 22 for measurement deviates from the blood vessel Ev as the measurement region. As a consequence, the measurement value become unstable. In this embodiment, this tracking operation in only one direction is performed by the blood vessel detection system behind the dichroic mirror 20 and the galvanometric mirror 15. The elements of the linear CCD 28 are arranged in the longitudinal direction of tracking light. When angle adjustment for the measurement region is completed, the fundus image Ea' in a one-dimensional direction perpendicular to the running direction of blood vessel Ev is enlarged and obtained. After the angle adjustment, the operator operates the operation lever of the input device 43 to move the indicator T in the direction indicated by the arrow in FIG. 5 and match the spot image M superimposed on tracking light with the measurement region, thereby selecting the measurement region. After the measurement region is determined, the operator operates the input device 43 again to input a tracking start command.

When the operator issues a tracking start command with the input device 43, the blood vessel position detection circuit 41 calculates the moving amount of the blood vessel image Ev' from a one-dimensional reference position on the basis of a light reception signal from the linear CCD 28. The blood vessel position detection circuit 41 then drives the galvanometric mirror 15 on the basis of this moving amount and controls to make the reception position of the blood vessel image Ev' on the linear CCD 28 constant. Upon checking the tracking state, the operator presses the operation switch again to start measurement. The system controller 42 then causes the memory to store continuous output signals from the photomultipliers 33a and 33b for a predetermined period of time, e.g., 2 sec. The stored output signals are then subjected to FFT conversion to calculate and display the maximum blood flow velocity by obtaining maximum Doppler shift amounts $\Delta fmax1$ and $\Delta fmax2$.

In papilla blood flow measurement, the operator selects a papilla measuring mode and inputs a corresponding signal to the system controller 42. Upon reception of this signal, the aperture switching mechanism 44 inserts the light shielding aperture 31 into the optical path in place of the cofocal aperture 30. The subsequent operation and the subsequent operation of each component are almost the same as those in intravascular blood flow measurement except that tracking is not performed. Only the difference between these measurements will therefore be described below.

Figure 8:
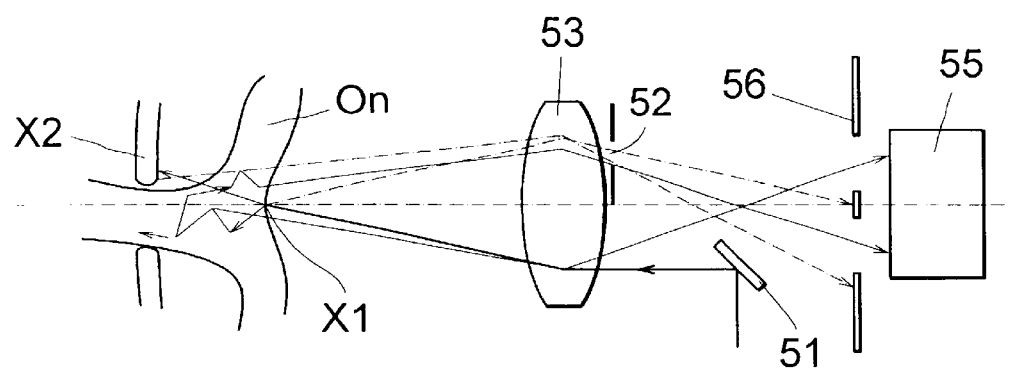
FIG. 8 is a view for explaining the function of the light shielding aperture.

The operator operates the input device 43 to guide measurement light to a measurement region in the papilla. When the operator presses the measurement switch afterward, the system controller 42 receives light reception signals from the photomultipliers 33a and 33b. The function of the light shielding aperture 31 at this time will be described with reference to FIG. 8.

In general, of a papilla on the fundus Ea as a measurement target, the region X1 having no major blood vessel becomes a measurement region. Since the optic nerves gathering in this papilla On extend to the brain through the pigment epithelium, a scattering region formed from a bundle of almost transparent optic nerves exists behind the region X1. Capillaries are scattered in this portion in random directions. In papilla measurement, a blood flow in this portion is a measurement target. A light beam from the laser diode 22 for measurement is incident on the mirror 51 from below and reflected to the left. The region X1 is then irradiated with this light. Reflected light from the region X1 passes through the opening 52 having the same function of determining a light receiving direction as that of the pair of mirrors 32a and 32b, and is blocked by a light shielding member 56 made conjugate to the region X1 by the lens 53. The light is then incident on the photomultiplier 55.

On the other hand, the measurement light scattered at the measurement region X2 indicated by the dotted line is formed into an image by the lens 53, like the light beam reflected by the region X1 indicated by the solid line. This measurement light passes through the ring-like portion in the center of the light shielding member 56 and strikes the photomultiplier 55.

Since this embodiment includes the light shielding aperture 31 having the same function as that of the light shielding member 56 described above, the direct reflected light from the region X1 which is incident on the papilla On is cut, and the measurement light scattered at the remaining regions, especially the measurement region S2 in the deep portion of the papilla, is incident on the photomultipliers 33a and 33b. The measurement signal from which a strong regularly reflected component from the papilla On is removed exhibits the high S/N of a Doppler signal component based on blood cells in the papilla On and little low-frequency fluctuations caused by ocular movement, thereby allowing stable measurement.

Figure 9A:
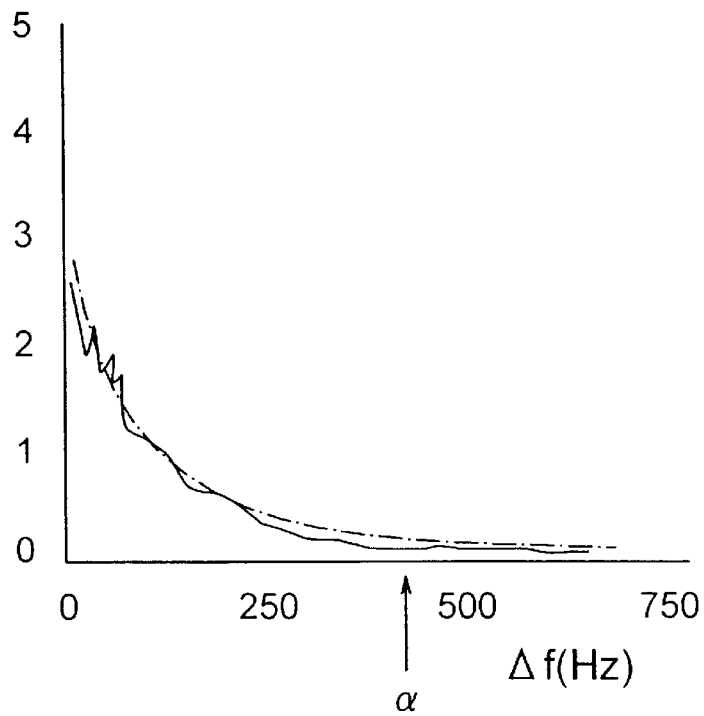
FIGS. 9A and 9B are graphs showing light reception signals having undergone frequency analysis.
Figure 9B:
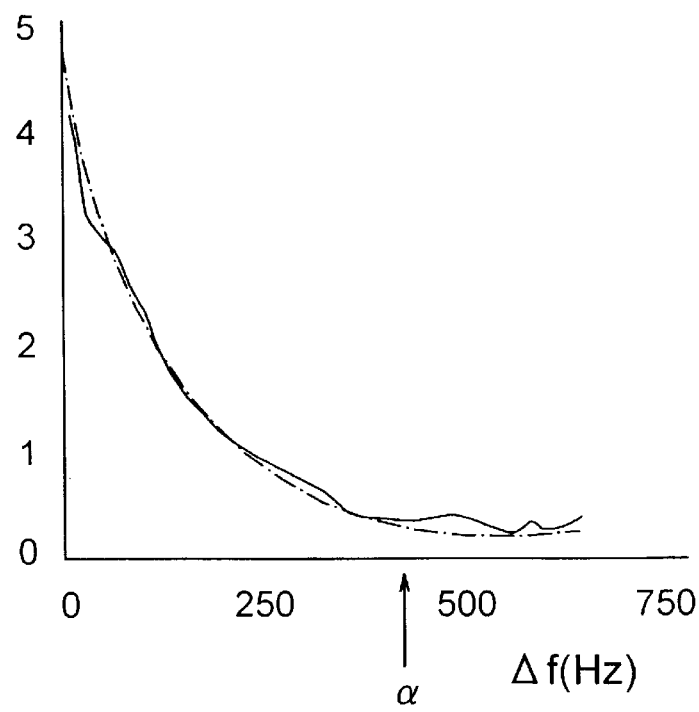
Figure 10:
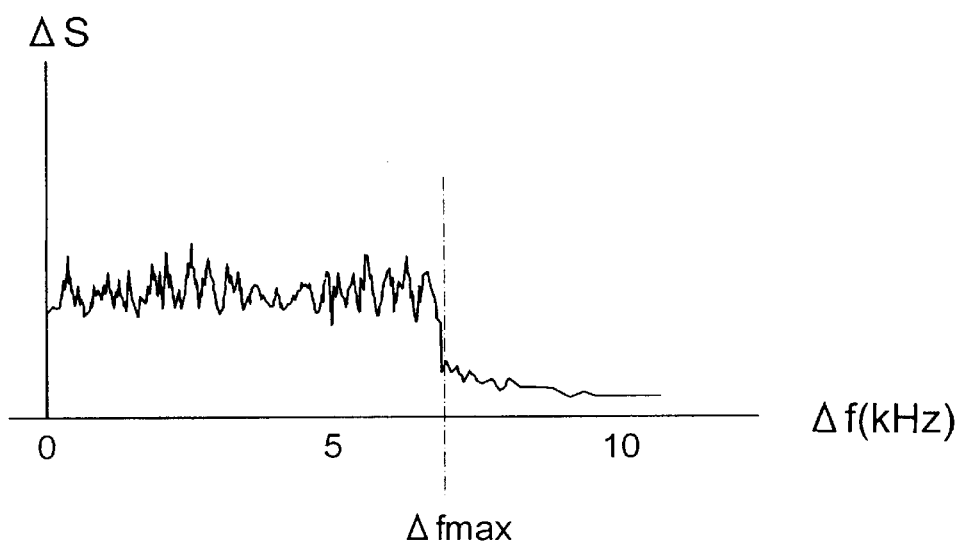
FIG. 10 is a graph showing a light reception signal having undergone frequency analysis.
Figure 11:
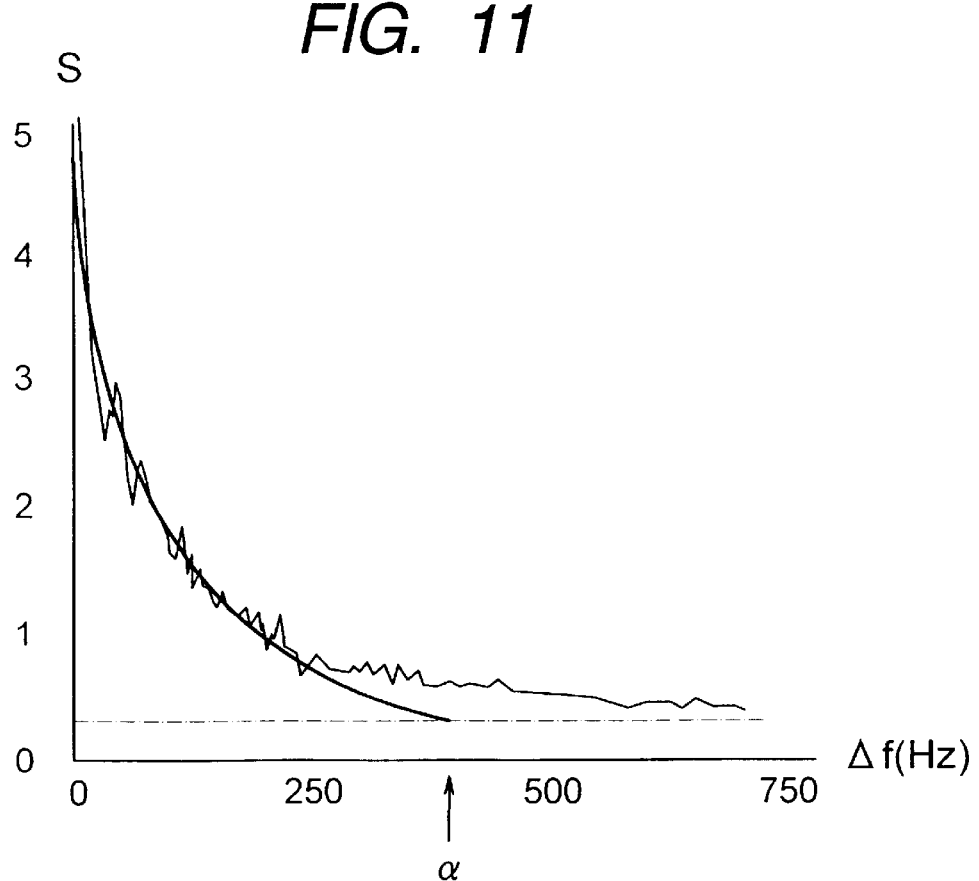
FIG. 11 is a graph showing a light reception signal having undergone frequency analysis.

FIGS. 9A and 9B show this state. FIG. 9A is a graph for comparison, which shows the analysis result obtained in the absence of the light shielding aperture 31. FIG. 9B shows the result obtained by the arrangement of this embodiment with the light shielding aperture 31. As compared with the curve in FIG. 9A, the curve in FIG. 9B exhibits high spectral intensity at low frequencies, in particular, and little disturbance, i.e., unevenness, and has a shape more similar to the broken line curve representing the result obtained upon fitting.

The light reception signals received by the photomultipliers 33a and 33b are light beams sufficiently scattered in the papilla On, and hence become almost identical to each other without dependence on the light receiving directions. The respective signals are stored by the system controller 42 and are approximated to equation (3) to calculate the average of coefficients, thereby calculating one blood flow velocity value per measurement.

According to the fundus blood flowmeter of this embodiment, it is possible to prevent the adverse effect of a regularly reflected component from the papilla in papilla measurement, i.e., a deterioration in the S/N of an AC component, and fluctuations due to ocular movement, and the frequency analysis result coincides with a logical model, thereby allowing stable measurement of a blood flow velocity in the papilla. In addition, this embodiment includes both the function of measuring an intravascular blood flow velocity on the fundus and the function of measuring a blood flow velocity in the papilla, and can selectively use these functions. This makes it possible to easily measure an intravascular blood flow velocity and a blood flow velocity in the papilla.

As has been described above, the fundus blood flowmeter according to the present invention makes a frequency analysis result match with a theoretical model, and can stably measure a blood flow velocity on the fundus. In addition, by selectively using the cofocal aperture and the light shielding aperture, an intravascular blood flow velocity and a blood flow velocity in the papilla can be easily measured.

What is claimed is:

1. An ophthalmologic measurement apparatus comprising:
   irradiation means for irradiating a fundus of an eye to be examined with coherent blood flow measurement beam;
   detection means for detecting scattered light of the measurement beam from the fundus;
   arithmetic means for calculating a blood flow velocity on the basis of a signal from said detection means; and
   a light shielding aperture for covering a region irradiated with the measurement beam at a position, substantially conjugate to the fundus, of said detection means.

2. An apparatus according to claim 1, further comprising:
   a cofocal aperture for shielding light other than scattered light from the irradiated region irradiated with the measurement beam at the position substantially conjugate to the fundus; and
   a switching mechanism for switching between said light shielding aperture and said cofocal aperture.

3. An apparatus according to claim 2, further comprising: mode switching means for switching between a first measuring mode of measuring a blood flow velocity in an optical nerve head and a second measuring mode of measuring a blood flow velocity in a blood vessel on the fundus,
   wherein said light shielding aperture and said cofocal aperture are switched in accordance with switching by said mode switching means.

4. An ophthalmologic measurement apparatus comprising:
   irradiation means for irradiating a fundus of an eye to be examined with coherent measurement beam;
   detection means for detecting scattered light of the blood flow measurement light from the fundus;
   arithmetic means for calculating a blood flow velocity on the basis of a signal from said detection means;
   a light shielding aperture for covering a region irradiated with the measurement beam at a position, substantially conjugate to the fundus, of said detection means,
   a cofocal aperture for shielding light other than scattered light from the irradiated region irradiated with the measurement beam at the position substantially conjugate to the fundus; and
   mode switching means for switching between a first measuring mode of measuring a blood flow velocity in an optical nerve head and a second measuring mode of measuring a blood flow velocity in a blood vessel on the fundus,
   wherein said light shielding aperture and said cofocal aperture are switched in accordance with switching by said mode switching means.

* * * * *